(12) United States Patent
Min et al.

(10) Patent No.: US 8,831,747 B1
(45) Date of Patent: Sep. 9, 2014

(54) LEADLESS NEUROSTIMULATION DEVICE AND METHOD INCLUDING THE SAME

(71) Applicant: Pacesetter, Inc., Sylmar, CA (US)

(72) Inventors: Xiaoyi Min, Camarillo, CA (US); Gabriel Mouchawar, Valencia, CA (US); Shiloh Sison, Alameda, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/084,471

(22) Filed: Nov. 19, 2013

(51) Int. Cl.
*A61N 1/00* (2006.01)
*A61N 1/375* (2006.01)
*A61N 1/36* (2006.01)
*A61N 1/378* (2006.01)

(52) U.S. Cl.
CPC .......... *A61N 1/3756* (2013.01); *A61N 1/36125* (2013.01); *A61N 1/3787* (2013.01)
USPC .......................................................... 607/117

(58) Field of Classification Search
USPC .................................................... 607/60, 117
See application file for complete search history.

(56) References Cited

U.S. PATENT DOCUMENTS

| | | | |
|---|---|---|---|
| 6,236,892 B1 | 5/2001 | Feler | |
| 6,445,953 B1 | 9/2002 | Bulkes et al. | |
| 6,462,348 B1 | 10/2002 | Gelbart | |
| 7,826,903 B2 | 11/2010 | Denker et al. | |
| 7,894,907 B2 | 2/2011 | Cowan et al. | |
| 7,899,542 B2 | 3/2011 | Cowan et al. | |
| 7,974,705 B2 | 7/2011 | Zdeblick et al. | |
| 8,204,605 B2 | 6/2012 | Hastings et al. | |
| 8,315,701 B2 | 11/2012 | Cowan et al. | |
| 8,340,780 B2 | 12/2012 | Hastings et al. | |
| 8,432,090 B2 | 4/2013 | Colard | |
| 8,478,408 B2 | 7/2013 | Hastings et al. | |
| 8,509,909 B2 | 8/2013 | Figueiredo et al. | |
| 2004/0010296 A1 | 1/2004 | Swanson et al. | |

(Continued)

FOREIGN PATENT DOCUMENTS

WO   WO 2012/138782 A1   10/2012

OTHER PUBLICATIONS

Shellock, et al. "Evaluation of Magnetic Resonance Imaging Issues for a Wirelessly Powered Lead Used for Epidural, Spinal Cord Stimulation," Neuromodulation 2013, pp. 1-6, 2013 International Neuromodulation Society.

(Continued)

*Primary Examiner* — Nicole F Lavert

(57) ABSTRACT

Leadless neurostimulation (NS) device including a device body and electrodes positioned along an active side of the device body. The electrodes form a multi-electrode array that is configured to interface with nervous tissue of a patient and supply electrical pulses to the nervous tissue. The NS device also includes an electronic sub-system that is coupled to the device body. The electronic sub-system includes switching circuitry, a power source, and an inductive coil that is operably coupled to the power source. The inductive coil is configured to receive electrical power through inductive coupling with an external coil. The device body, including the inductive coil coupled thereto, is sized and shaped to be disposed within an epidural space of a patient.

20 Claims, 7 Drawing Sheets

(56) References Cited

U.S. PATENT DOCUMENTS

| | | |
|---|---|---|
| 2010/0057165 A1 | 3/2010 | Moffitt et al. |
| 2011/0054565 A1* | 3/2011 | Wacnik et al. ............... 607/46 |
| 2011/0112610 A1 | 5/2011 | Rahman et al. |
| 2011/0118810 A1 | 5/2011 | Cowan et al. |
| 2011/0125223 A1 | 5/2011 | Carbunaru et al. |
| 2012/0283800 A1 | 11/2012 | Perryman et al. |
| 2012/0330384 A1 | 12/2012 | Perryman et al. |
| 2013/0066400 A1 | 3/2013 | Perryman et al. |
| 2013/0079849 A1 | 3/2013 | Perryman et al. |

OTHER PUBLICATIONS

Perryman, et al. "Injectable spinal cord stimulator system: Pilot study," Techniques in Regional Anesthesia and Pain Management 16 (2012) pp. 102-105, 2013 Elsevier Inc.

Suaning, et al. "CMOS Neurostirnulation ASIC with 100 Channels, Scaleable Output, and Bidirectional Radio-Frequency Telemetry," IEEE Transactions on Biomedical Engineering, vol. 48, No. 2, Feb. 2001, pp. 248-260, 2001 IEEE.

* cited by examiner

| 402 | POSITION ELECTRODES TO FORM A MULTI-ELECTRODE ARRAY |
| 404 | PROVIDE ELECTRONIC SUB-SYSTEM AND POSITION RELATIVE TO THE MULTI-ELECTRODE ARRAY |
| 406 | ELECTRICALLY COUPLE THE ELECTRODES TO THE ELECTRONIC SUB-SYSTEM THROUGH WIRE CONDUCTORS |
| 408 | FORM A LEAD BODY THAT AT LEAST PARTIALLY SURROUNDS THE ELECTRONIC SUB-SYSTEM, ELECTRODES, AND WIRE CONDUCTORS |

LEADLESS NEUROSTIMULATION DEVICE AND METHOD INCLUDING THE SAME

BACKGROUND

The subject matter described herein generally relates to neurostimulation (NS) systems and NS devices for generating electric fields proximate to nervous tissue.

NS systems are configured to generate electrical pulses and deliver the pulses to nervous tissue to treat a variety of disorders. Spinal cord stimulation (SCS) is a common type of neurostimulation. In SCS, electrical pulses are delivered to nervous tissue in the spine to generate electric fields that can treat a neurologic condition. For example, the application of an electric field to spinal nervous tissue can effectively mask or alleviate certain types of pain transmitted from regions of the body associated with the stimulated nervous tissue.

Conventional NS systems may include a pulse generator and one or more elongated leads that are electrically coupled to the pulse generator. Each elongated lead includes a stimulating end, a trailing end, and an intermediate portion that couples the stimulating and trailing ends. The elongated lead may be cable-like and extend, for example, up to sixty centimeters or more between the stimulating and trailing ends. The stimulating end may have a body with multiple electrodes that are configured to interface with nervous tissue, such as within an epidural space of a spinal cord. The trailing end includes multiple terminal contacts that engage corresponding contacts of the pulse generator. The terminal contacts of the trailing end and the electrodes of the stimulating end are coupled by wire conductors that extend through the intermediate portion. In use, the pulse generator controls current through the wire conductors to generate the electric fields along the nervous tissue. The pulse generator is typically implanted within the patient in a subcutaneous pocket formed near the surface of the skin. The pulse generator may be programmed (and re-programmed) to provide the electrical pulses in accordance with a designated sequence.

Typically, one of two types of leads is used. The first type is a percutaneous lead, which has a rod-like shape and includes electrodes spaced apart from each other along a single axis. The second type of lead is a laminectomy or laminotomy lead (hereinafter referred to as a paddle lead). A paddle lead may have an elongated and generally planar body with a substantially rectangular shape (i.e., paddle-like shape). Paddle leads typically include an array of electrodes that are spaced apart from each other. The number of electrodes may be, for example, four, eight, sixteen, or more.

Although such NS systems can be effective for treating one or more neurologic conditions, some drawbacks or challenges may exist. For example, NS systems may be prone to heating and induced currents when placed within strong gradient and/or radiofrequency (RF) magnetic fields of a magnetic resonance imaging (MRI) system. The heat and induced currents result from the metal components of the leads functioning as antennas in the magnetic fields. Components of the system may also move due to the force/torque generated in the static magnetic field of an MRI system.

In addition to the above, the number of components and overall shape and size of a conventional NS system may increase the likelihood of infection or require a follow-up surgery for the patient. For instance, in order to implant the entire NS system, the elongated lead is tunneled from the epidural space through the body and into the subcutaneous pocket where the pulse generator is located. NS systems that do not require tunneling and a subcutaneous pocket may reduce the likelihood of infection and/or a follow-up procedure being necessary.

BRIEF SUMMARY

In accordance with an embodiment, a leadless neurostimulation (NS) device is provided that includes a device body having opposite first and second ends and an active side that extends between the first and second ends. The NS device also includes electrodes forming a multi-electrode array along the active side of the device body. The multi-electrode array is configured to interface with nervous tissue in an epidural space of a patient and generate electric fields along the nervous tissue. The NS device also includes an electronic sub-system provided within the device body. The electronic sub-system includes switching circuitry, a power source, and an inductive coil operably coupled to the power source. The electronic sub-system is configured to provide electrical pulses to the multi-electrode array for generating the electric fields. The inductive coil is configured to receive electrical power through inductive coupling with an external coil to charge the power source. The device body, including the inductive coil coupled thereto, is sized and shaped to be disposed within the epidural space of the patient.

In some embodiments, the NS device may be a wireless lead that is configured to be disposed entirely within the epidural space. For example, the inductive coil may also be configured to communicate data with an external monitoring system. In particular embodiments, the device body may be a low-profile substantially planar body that coincides with lateral and longitudinal axes that are perpendicular to each other. In such cases, the inductive coil may be substantially planar and extending along the lateral and longitudinal axes.

In an embodiment, a leadless neurostimulation (NS) device is provided that includes a device body having opposite first and second ends and an active side that extends between the first and second ends. The NS device also includes electrodes forming a multi-electrode array along the active side of the device body. The multi-electrode array is configured to interface with nervous tissue in an epidural space of a patient and generate electric fields along the nervous tissue. The NS device also includes an electronic sub-system provided within the device body and wire conductors that extend through the device body and electrically couple the multi-electrode array to the electronic sub-system. The electronic sub-system is configured to control the electrodes to generate electric fields proximate to the nervous tissue, wherein the device body, including the electronic sub-system, is sized and shaped to be disposed within an epidural space of the patient.

In an embodiment, a method of manufacturing a leadless neurostimulation (NS) device is provided. The method includes positioning electrodes with respect to each other to form a multi-electrode array and providing an electronic sub-system including switching circuitry, a power source, and an inductive coil that is operably coupled to the power source. The method also includes electrically coupling the electrodes to the electronic sub-system through wire conductors and forming a device body that at least partially surrounds the switching circuitry, the power source, and the inductive coil. The electrodes are positioned along an active side of the device body. The device body, the switching circuitry, the power source, and the inductive coil are collectively sized and shaped to be disposed within an epidural space of a patient.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

DETAILED DESCRIPTION

Figure 1:
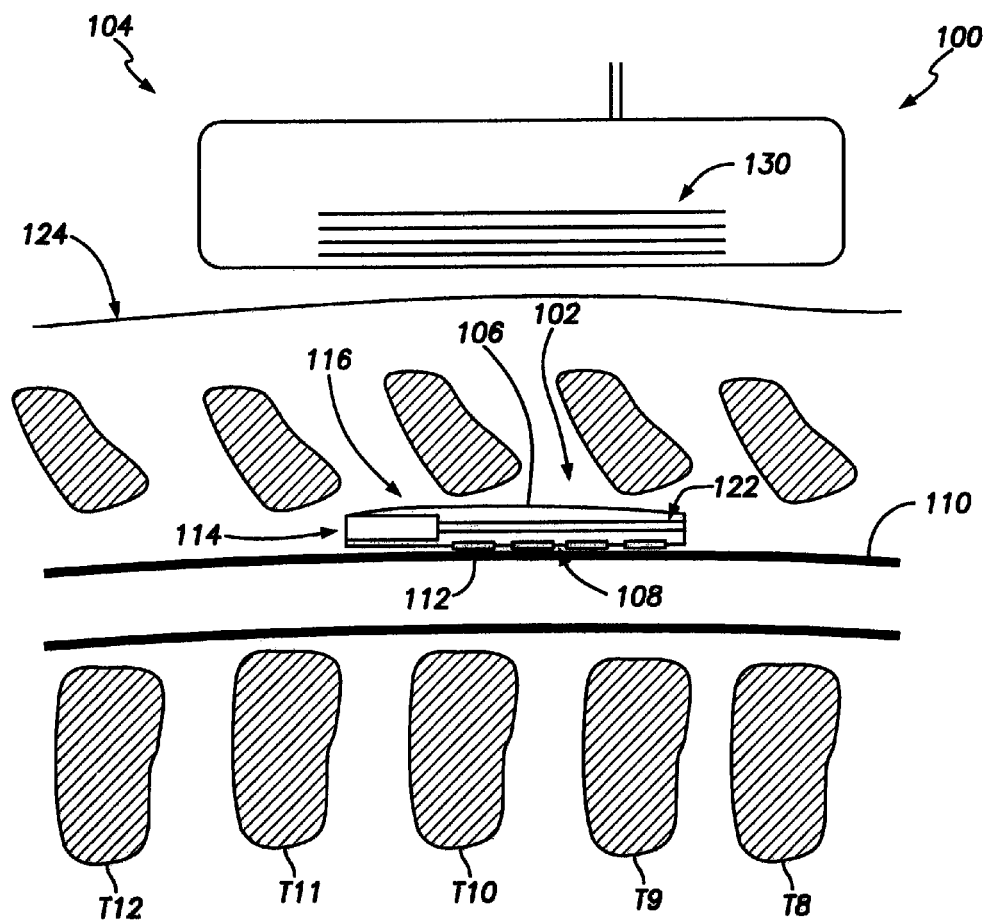
FIG. 1 is a side view of a neurostimulation (NS) system for applying electric fields to nervous tissue of a patient in accordance with one embodiment.

Embodiments described herein include neurostimulation (NS) leads, NS systems, and methods of manufacturing or using the same. The NS devices may be configured to be inserted into a space or cavity of a patient and positioned adjacent to nervous tissue. In certain embodiments, the NS devices are wireless leads that are positioned entirely within an epidural space of a spinal column. The NS devices may include an implantable device body having an electronic sub-system (or pulse generator) and an array of electrodes operably coupled to the electronic sub-system. The electronic sub-system may include, for example, one or more current/voltage sources, switching circuitry, and a power source. The electronic sub-system is configured to generate electric fields with the electrodes for providing a therapeutic stimulation. In particular embodiments, the electronic sub-system interacts with an external monitoring system through inductive coupling. For instance, embodiments may interact through inductive coils, which may also be referred to as primary or secondary coils depending upon the function of the coil. During operation, the primary and secondary coils may at least one of communicate data (e.g., pulse data) or transmit/receive electrical power.

The device body may have a shape that is similar to percutaneous or paddle NS devices. For example, the device body may have an active side that interfaces with the nervous tissue and includes the electrodes positioned therealong. The electrodes are operably coupled to the electronic sub-system and may be selectively controlled to generate the electric fields near the nervous tissue. Collectively, the electrodes may form a multi-electrode array in which the electrodes may have one of a plurality of states during operation of the NS device. More specifically, one or more of the electrodes may function as a source (e.g., anode), one or more of the electrodes may function as a sink (e.g., cathode), and one or more of the electrodes may be inoperative due to, for example, a high impedance. In some embodiments, each of the electrodes is selectively controlled such that each electrode is capable of functioning as a source, sink, or inoperative element over the lifetime of the NS device.

The electronic sub-system may include one or more current/voltage sources and switching circuitry that are coupled to the device body and located proximate to the electrodes located along the active side of the device body. In some embodiments, the electronic sub-system is electrically coupled to each of the electrodes of the array (or a sub-array of the array) through a single wire conductor. As such, the switching circuitry may selectively control each of the electrodes, via the respective wire conductor, to operate as an anode or cathode or as an inoperative element. In other embodiments, the electronic sub-system may be electrically coupled to each of the electrodes of the array (or sub-array) through multiple wire conductors. The wire conductors may include, for example, a control line, a power line, and a ground line that are each coupled to multiple electrodes. In such embodiments, each of the electrodes may include circuitry for controlling the state of the electrode.

In particular embodiments, the multi-electrode array may be a two-dimensional array that provides electrode coverage comparable to known paddle leads. As used herein, the term "two-dimensional array" is not intended to limit the array to a strictly planar configuration. Instead, two-dimensional arrays may move in and out of a plane when, for example, the device body bends in the epidural space. In some embodiments, the device body may be manufactured to have a non-planar contour such that the two-dimensional array has a non-planar configuration.

For embodiments that include two-dimensional arrays, the active side of the wireless lead may extend generally along a lateral axis and a longitudinal axis that are perpendicular to each other. Dimensions of the two-dimensional array may permit multiple electrodes to be distributed along the lateral axis and multiple electrodes to be distributed along the longitudinal axis. The electrodes may have a grid or matrix configuration such that the electrodes are positioned in substantially linear rows and columns. For instance, the multi-electrode array may be configured to have a coverage similar to Penta™ paddle leads distributed by St. Jude Medical. In other embodiments, however, the electrodes of the two-dimensional array may not be arranged in substantially linear rows and columns.

In certain embodiments, the inductive coil of the NS device may extend generally along a coil plane that coincides with the multi-electrode array or that is parallel to an array plane that coincides with the multi-electrode array. The secondary coil may have multiple turns and form a designated coil area in order to effectively communicate data and/or receive electrical power when disposed within the epidural space. For example, the inductive coil may be configured to inductively couple with a primary coil in a sufficient manner when separated about three to six centimeters from the primary coil.

FIG. 1 depicts a NS system 100 that includes an implantable NS device 102 and an external monitoring system 104 configured to communicate with and power (e.g., charge) the NS device 102. The NS device 102 has a device body 106 including an active side 108 that interfaces with nervous tissue 110 of a patient in an epidural space 116. In the illustrated embodiment, the nervous tissue 110 is spinal cord tissue (e.g., dorsal column (DC) fibers and/or dorsal root (DR) fibers). The active side 108 includes a plurality of electrodes 112 that are configured to generate electric fields proximate to the nervous tissue 110. As shown in FIG. 1, the nervous tissue 110 engaged by the active side 108 includes the spinal cord along the thoracic vertebra T9 and T10. The active side 108 interfaces with the dura mater of the spinal column. The cerebrospinal fluid and nerve fibers, which are surrounded by the dura mater, are not shown in FIG. 1. However, it is noted that FIG. 1 shows only one application of the NS device 102. It is understood that embodiments may be used in other neurostimulating applications.

Figure 2:
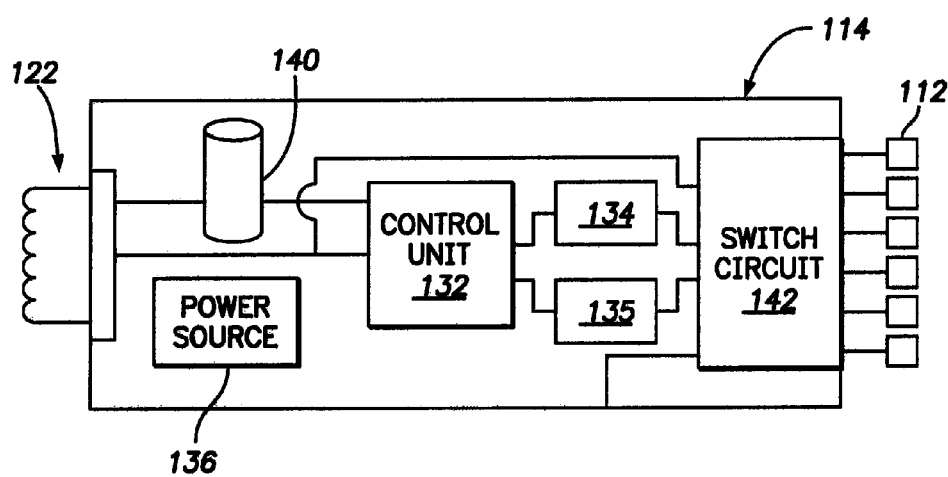
FIG. 2 is a schematic diagram of a NS device in accordance with one embodiment, which may be used with the NS system of FIG. 1.

The NS device 102 includes an electronic sub-system 114, which may also be referred to as a pulse generator. The electronic sub-system 114 is configured to control operation of the NS device 102 and interact with the monitoring system 104. For example, as shown in FIG. 2, the electronic sub-system 114 may include a control unit 132, one or more current/voltage sources 134, 135, a power source 136, an inductive coil (or antenna) 122, memory 140, and switching circuitry 142. Unlike known NS devices, the electronic sub-system 114 may be disposed within the epidural space 116 of the patient with the device body 106. For example, as shown in FIG. 1, the NS device 102 is dimensioned (e.g., sized and shaped) such that the entire NS device 102 is located within the epidural space 116, including the entire electronic sub-system 114. In other embodiments, one or more portions of the NS device 102 may extend out of the epidural space 116. For example, at least one of the control unit 132, the current/voltage sources 134, 135, the power source 136, the inductive coil (or antenna) 122, or the memory 140 may at least partially tunnel through the body of the patient toward a skin surface 124 of the patient.

When the NS device 102 is disposed within the epidural space 116 and used by the patient, the NS device 102 may interact with the monitoring system 104. For example, the monitoring system 104 and the NS device 102 may communicate with each other one or more times after the NS device 102 has been implanted. At later intervals (e.g., once a week, twice a month, once every two months, and the like), the monitoring system 104 and the NS device 102 may interact with each other to (i) communicate data between the NS device 102 and the monitoring system 104 and/or (b) charge the power source 120.

To this end, the monitoring system 104 may also include an inductive coil 130. The inductive coil 130 may be referred to as a primary coil, and the inductive coil 122 may be referred to as a secondary coil. The inductive coil 130 may be sized and shaped to be larger than the inductive coil 122. In some embodiments, the inductive coils 122, 130 may (a) communicate data for operating and monitoring conditions of the NS device 102 in the patient and (b) electrically power or charge the NS device 102. In other embodiments, however, at least one of the monitoring system 104 or the NS device 102 may include more than one inductive coil in which each inductive coil has separate functions. For example, one inductive coil may be used to communicate data and another inductive coil may be used to transmit/receive electrical power.

FIG. 2 is a schematic diagram illustrating components of the electronic sub-system 114 of the NS device 102 (FIG. 1). As shown, the electronic sub-system 114 includes the control unit 132, the current/voltage sources 134, 135, the power source 136, the inductive coil (or antenna) 122, the memory 140, and the switching circuitry 142, which may also be characterized as a switch array, switch matrix, or multiplexer. One or more components may be part of or include another component. For instance, the switching circuitry 142 may include the current/voltage sources 134, 135 and/or the switching circuitry 142 and the current/voltage sources 134, 135 may be part of the same hardware unit. Although not shown, the electronic sub-system may include additional components or circuitry for operating the NS device in designated manner (e.g., regulators, capacitors, resistors, transistors, and the like).

As shown, the control unit 132, the current/voltage sources 134, 135, and the switching circuitry 142 are illustrated as separate blocks. It is understood, however, that such distinctions are not necessarily indicative of the division between hardware circuitry. Thus, for example, one or more of the functional blocks (e.g., control unit, the current/voltage sources, switching circuitry, memory) may be implemented in a single piece of hardware or through multiple pieces of hardware. The electronic sub-system 114 and its components may control the various modes for providing stimulation therapy and, optionally, monitoring such stimulation therapy. More specifically, it is to be understood that the different functions or operations described herein that are performed by the electronic sub-system 114 and its components (e.g., the control unit 132, the current/voltage sources 134, 135, the power source 136, the inductive coil 122, the memory 140, and the switching circuitry 142) may be implemented using hardware with associated instructions (e.g., software stored on a tangible and non-transitory computer readable storage medium, such as a computer hard drive, ROM, RAM, or the like) that perform the functions/operations described herein. The hardware may include state machine circuitry hard wired to perform the functions/operations described herein. Optionally, the hardware may include electronic circuits that include and/or are connected to one or more logic-based devices, such as microprocessors, processors, controllers, or the like. Optionally, the components may include processing circuitry such as one or more field programmable gate array (FPGA), application specific integrated circuit (ASIC), or microprocessor. The components in various embodiments may be configured to execute one or more algorithms to perform functions described herein. The one or more algorithms may include aspects of embodiments disclosed herein, whether or not expressly identified in a flowchart or a method.

The inductive coil 122 may be operatively coupled to the control unit 132, the current/voltage sources 134, 135, the power source 136, the memory 140, and the switching circuitry 142. In some embodiments, the inductive coil 122 is configured to receive signals (e.g., instructions or other data) from the monitoring system 104 (FIG. 1) and communicate the signals to the control unit 132, the memory 140, or other components. The signals may include, for example, software updates, updated stimulation sequences, data regarding conditions of the NS device 102 or the patient, and the like. The inductive coil 122 may also be configured to receive electrical power from the monitoring system 104 and transfer the electrical power to the power source 136.

In some embodiments, the power source 136 may be a rechargeable power source, such as a lithium ion rechargeable (LIR) battery. By way of example only, the capacity of the power source may be from about 20 mAh to about 180 mAh with a nominal voltage of about 3.60V. Examples of suitable LIR batteries includes Eagle Picher LIR 2025, 2430, 2450 and the like or Quallion QL0003I. In some embodiments, the power source may be capable of operating between one week to one month (or more) between charges with about a 100-150 μA stimulation current drain. In addition to supplying the power for transmitting electrical pulses during neurostimulation, the power source 136 may be used to control other functions of the electronic sub-system 114.

The current/voltage sources 134, 135 may be operably coupled to the electrodes 112 through the switching circuitry 142. Each of the current/voltage sources 134, 135 may be single- or multi-channel and be capable of delivering a single stimulation pulse or multiple stimulation pulses. In some embodiments, the current/voltage sources 134, 135 and the switching circuitry 142 can be configured to deliver stimulation pulses to multiple channels on a time-interleaved basis, in which case the switching circuitry 142 can time division multiplex the output of current/voltage sources 134, 135 across different electrode combinations at different times to deliver multiple programs or channels of stimulation energy to the patient.

The control unit 132 can control the current/voltage sources 134, 135 and the switching circuitry 142 to generate electric fields in accordance with parameters specified by one or more neurostimulation parameter sequences (or protocols) stored within the memory 140. Exemplary parameters for the electrical pulses may include a pulse amplitude, pulse width, and pulse rate for a stimulation waveform. Additionally, the control unit 132 can control the switching circuitry 142 to select different electrode configurations for generating the designated electric fields. Each electrode 112 can be connected as an anode, a cathode, or an inoperative electrode (in which case the electrode is not used for transmitting energy, i.e., is inactive).

For implementation of the components within NS devices set forth herein, the control unit, current/voltage sources, memory, and switching circuitry may be similar to or function in a similar manner as the components described in U.S. Patent Application Publication No. 2006/0259098, entitled "SYSTEMS AND METHODS FOR USE IN PULSE GENERATION," which is incorporated herein by reference in its entirety. Circuitry for recharging the power source of the NS device using inductive coupling and external charging circuits are described in U.S. Pat. No. 7,212,110, entitled "IMPLANTABLE DEVICE AND SYSTEM FOR WIRELESS COMMUNICATION," which is incorporated herein by reference in its entirety. One or more NS devices may be similar to paddle leads described in U.S. Patent Application Publication No. US 2013/0006341, which is incorporated herein by reference in its entirety.

In addition to the above, an example and discussion of "constant current" pulse generating circuitry is provided in U.S. Patent Application Publication No. 2006/0170486 entitled "PULSE GENERATOR HAVING AN EFFICIENT FRACTIONAL VOLTAGE CONVERTER AND METHOD OF USE," which is incorporated herein by reference in its entirety. One or multiple sets of such circuitry may be provided within the NS device 102. Different pulses on different electrodes may be generated using a single set of pulse generating circuitry using consecutively generated pulses according to a "multi-stimset program." Complex pulse parameters may be employed such as those described in U.S. Pat. No. 7,228,179, entitled "METHOD AND APPARATUS FOR PROVIDING COMPLEX TISSUE STIMULATION PATTERNS," and International Patent Publication No. WO 2001/093953 A1, entitled "NEUROMODULATION THERAPY SYSTEM," each of which is incorporated herein by reference in its entirety. Although constant current pulse generating circuitry is contemplated for some embodiments, any other suitable type of pulse generating circuitry may be employed such as constant voltage pulse generating circuitry.

The control unit 132 may control operation of the NS device pursuant to designated stimulation protocols. Each stimulation protocol may include one or more sets of stimulation parameters including pulse amplitude, pulse width, pulse frequency or inter-pulse period, pulse repetition parameter (e.g., number of times for a given pulse to be repeated for respective stimset during execution of program), etc. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 3:
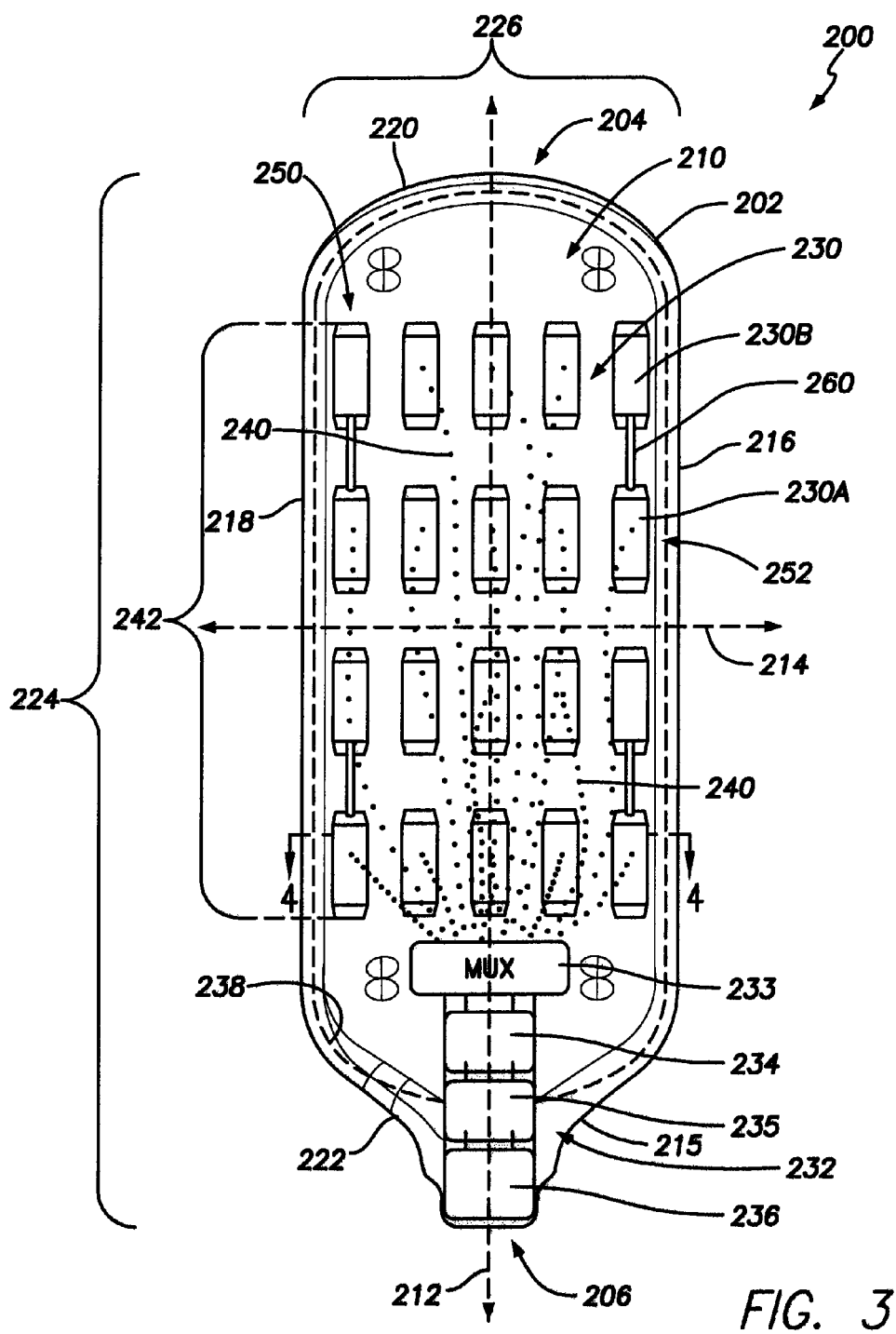
FIG. 3 illustrates a plan view of a wireless NS device formed in accordance with one embodiment that may be used with the NS system of FIG. 1.

FIG. 3 is a plan view of a NS device 200 formed in accordance with one embodiment. The NS device 200 may be similar or identical to the NS device 102 (FIG. 1) and be configured to interact with a monitoring system, such as the monitoring system 104 (FIG. 1). The NS device 200 may include a device body 202 having first and second body ends 204, 206. A first body side 208 (shown in FIG. 4) and a second body side 210 of the device body 202 extend between the body ends 204, 206. The body side 208 may be referenced as the active side of the device body 202 and is configured to interface with nervous tissue. As shown, the device body 202 is oriented with respect to a longitudinal axis 212 and a lateral axis 214 that are perpendicular with respect to each other.

The device body 202 may have a profile or perimeter that is defined by an outer lead edge 215. The lead edge 215 may include longitudinal edges or segments 216, 218 that extend generally parallel to the longitudinal axis 212, and lateral edges or segments 220, 222 that extend between and join the longitudinal edges 216, 218. In some embodiments, the lateral edges 220, 222 do not extend linearly between the longitudinal edges 216, 218 and, instead, may be curved or rounded. In the illustrated embodiment, the NS device 200 is a paddle lead. The device body 202 may be substantially planar and have a substantially rectangular profile or perimeter. However, the device body may have different profiles and shapes in other embodiments. For example, the end 216 may extend further away from a main portion of the device body 202 or the profile may be closer to a square shape than an elongated rectangle.

As shown, the device body 202 has a first dimension or length 224 that is measured along the longitudinal axis 212 and a second dimension or width 226 that is measured along the lateral axis 214. By way of example only, the length 224 may be about 20 to about 40 mm and the width 226 may be about 5 to about 15 mm. However, FIG. 2 illustrates only one embodiment of the NS device 200 and the device body 202 may have different dimensions in other embodiments.

The NS device 200 also includes electrodes 230 and an electronic sub-system 232 that are coupled to the device body 202. In the illustrated embodiment, the electrodes 230 and the electronic sub-system 232 are at least partially embedded within the device body 202. The electrodes 230 are positioned along the active side 208 (shown in FIG. 3) in a designated configuration. For illustrative purposes, the device body 202 is transparent so that the electrodes 230 and the electronic sub-system 232 are visible. It is understood that such components may not be visible through the body side 210 in the fully formed NS device.

The electronic sub-system 232 includes switching circuitry 233, a current/voltage source 234, a control unit 235, a power source 236, and an inductive coil 238, although additional elements may be included in other embodiments. The components of the electronic sub-system 232 may include features and operate in a similar manner as the components of the electronic sub-system 114 (FIG. 1).

The device body 202 may comprise one or more materials for supporting the electrodes 230 and other components, such as the switching circuitry 233, current/voltage sources 234, control unit 235, power source 236, and inductive coil 238. For example, the device body 202 may include one or more insulative materials and/or biocompatible materials. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The device body 202 may include a combination of materials. For example, portions of the device body 202 that are designated to be more flexible may comprise a more flexible material (e.g., silicone rubber and/or the like) and portions of the device body 202 that are designated to be more resilient may be a harder material (e.g., PEEK and/or a metal material). The NS device 200 may be manufactured using various processes, such as cutting, etching, or molding. In some embodiments, the NS device 200 is partially flexible or bendable in order to confirm to the anatomical structures within the epidural space. In particular embodiments, the NS device 200 may be shaped to complement the anatomical structures within the epidural space such that the NS device 200 partially surrounds the spinal column.

The electrodes 230 are electrically coupled to the electronic sub-system 232 or, more specifically, the switching circuitry 233 through a plurality of wire conductors 240 (indicated by dashed or broken lines). In some embodiments, the wire conductors 240 may include conductive material that is surrounded by a respective insulation layer or jacket. The wire conductors 240 may extend through the material of the device body to directly couple the electronic sub-system 232 to the electrodes 230. In the illustrated embodiment, some of the electrodes 230 are directly coupled to the switching circuitry 233 through a single wire conductor 240. As set forth herein, other embodiments may include electrodes that are electrically coupled to the same wire conductors. In such embodiments, the electrodes may include additional circuitry or logic for receiving and processing control signals that are transmitted through the wire conductors.

The electrodes 230 form a multi-electrode array 242 that is configured to generate electric fields proximate to nervous tissue. For example, the electrodes 230 may be controlled by the electronic sub-system 232 to operate or function as anodes, cathodes, or inactive elements. In some embodiments, the electrodes 230 may include base electrodes 230A and common electrodes 230B. The base electrodes 230A are electrically coupled to the switching circuitry 233 through corresponding wire conductors 240. The common electrodes 230B are coupled to the wire conductors 240 through the base electrodes 230A and bridge conductors 260. The bridge conductors 260 may be similar to the wire conductors 240, but extend through the device body 202 directly between a base electrode 230A and a corresponding common electrode 230B. During operation, the common electrode 230B has the same operating state (e.g., source, sink, or inactive) as the base electrode 230A to which the common electrode 230B is electrically coupled.

As shown, the multi-electrode array 242 may be a two-dimensional array such that multiple electrodes 230 are distributed along the width 226 (or the lateral axis 214) and multiple electrodes 230 are distributed along the length 224 (or the longitudinal axis 212). In the illustrated embodiment, the multi-electrode array 242 includes a plurality of columns 250 and a plurality of rows 252 in which the electrodes 230 of a designated column or row are aligned with one another. As such, the multi-electrode array 242 may form an electrode grid or matrix. However, two-dimensional arrays are not required to have such configurations. Instead, the electrodes of a two-dimensional array may have any location within an area covered by the array.

As shown, the electronic sub-system 232 may be positioned proximate to the multi-electrode array 242. Unlike conventional NS systems that couple the pulse generator and the electrodes through an elongated cable, the electronic sub-system 232 may be coupled to the same main body or structure (e.g., the device body 202) that supports the electrodes 230. More specifically, in the illustrated embodiment, the portion of the NS device 200 that provides the "paddle" shape of the NS device 200 supports the multi-electrode array 242 and the electronics that control generation of the electric fields.

Also shown in FIG. 3, the inductive coil 238 may be operably coupled to the other components of the electronic sub-system 232. As used herein, the term "operably coupled" includes two components being connected in a manner that enables or permits the two components to operate as described herein. Operably coupled components may be directly connected (e.g., physically connected) or indirectly connected through other elements. For example, the inductive coil 238 and the power source 236 are operably coupled in some embodiments such that the power source 236 can be charged through inductive coupling of the inductive coil 238 and an external or primary coil (not shown).

In the illustrated embodiment, the inductive coil 238 extends along the lead edge 215 of the device body 202. The inductive coil 238 is illustrated in FIG. 3 as a single dashed line. It is understood, however, that the inductive coil 238 may have multiple turns or windings that extend along a path shown in FIG. 3. More specifically, the inductive coil 238 may extend along a perimeter of the NS device 200. For example, the inductive coil 238 extends along a path as indicated in FIG. 3. A majority of the path may extend alongside (e.g., adjacent to) the lead edge 215 or, more specifically, the longitudinal edges 216, 218 and the lateral edges 220, 222 of the device body. In some embodiments, more than 60% of the path may extend adjacent to the lead 215. In particular embodiments, more than about 75% of the path may extend adjacent to the lead 215 or, more particularly, greater than about 90% of the path may extend adjacent to the lead 215.

Based on the configuration of the path taken by the inductive coil 238, the inductive coil 238 may define a designated coil area. The coil area defined by the inductive coil 238 may determine, in part, an efficiency in charging the NS device 200 through inductive coupling and/or an efficiency of communicating data with the NS device 200 through inductive coupling. In the illustrated embodiment, the coil area is substantially rectangular with the largest dimension extending along the longitudinal axis 212. However, other shapes for the coil area may be used. By way of example only, the coil area may be about 3 cm².

As shown in FIG. 3, the inductive coil 238 surrounds the entire multi-electrode array 242. More specifically, the length and width of the inductive coil 238 are greater than the length and width of the multi-electrode array 242. In other embodiments, the length and/or the width of the inductive coil 238 may be smaller than the corresponding dimension(s) of the multi-electrode array 242. In such cases, the inductive coil 238 may only surround a sub-array of the multi-electrode array 242. For example, the multi-electrode array 242 includes four rows 252 and five columns 250 in FIG. 3. In some embodiments, the inductive coil 238 may only surround three rows 252 and/or only surround four columns 250.

In other embodiments, the inductive coil 238 may be larger than shown in FIG. 3 without increasing the number of electrodes 230. More specifically, the device body 202 may be enlarged in order to increase the size of the coil area. For instance, the length 224 may be increased so that the inductive coil 238 defines a greater coil area. Yet still in other embodiments, the inductive coil 238 may not surround the multi-electrode array 242. For example, the inductive coil 238 may only surround the other components of the electronic subsystem 232 (e.g., the switching circuitry 233, the current/voltage source 234, and the power source 236).

The NS device 200 may be a wireless lead that is dimensioned (e.g., sized and shaped) so that the NS device 200 is capable of being disposed within the epidural space of the spinal column. By way of example only, the NS device 200 may have a length 224 of about 30.0 mm and a width 226 of about 11.0 mm. The NS device 200 may have larger or smaller lengths and widths in other embodiments. The NS device 200 may also have a thickness 225 (shown in FIG. 4) of about 1.0 to about 4.0 mm. As such, the entire NS device 200 may be disposed within the epidural space.

In some embodiments, with the reduced overall size and the lack of wire conductors extending between an outer pulse generator and the inner device body, the NS device 200 may result in fewer complications (e.g., infection or complexities of surgery) with respect to other known leads. However, it is understood that other embodiments may include NS devices with portions that extend out of the epidural space. For example, a portion of the device body 202 may be tunneled out of the epidural space. This external portion may be shaped to hold, for example, part of the inductive coil.

Figure 4:
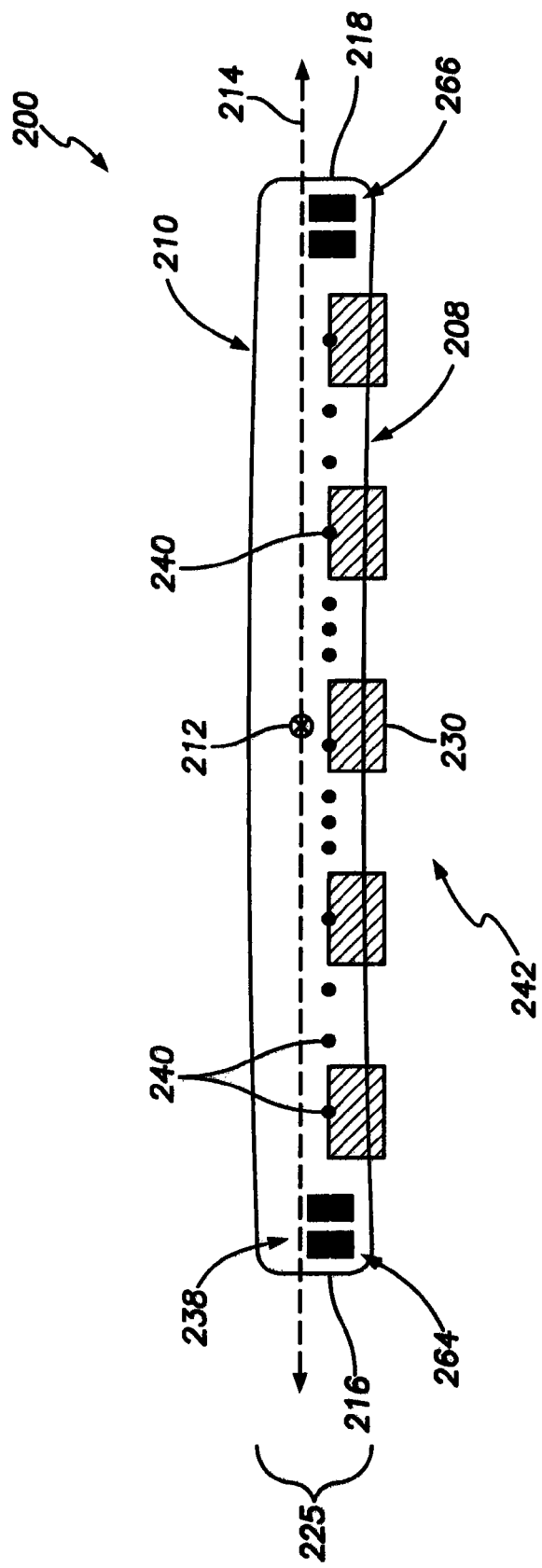
FIG. 4 is a cross-section of the NS device taken along the lines 4-4 in FIG. 3.
Figure 5:
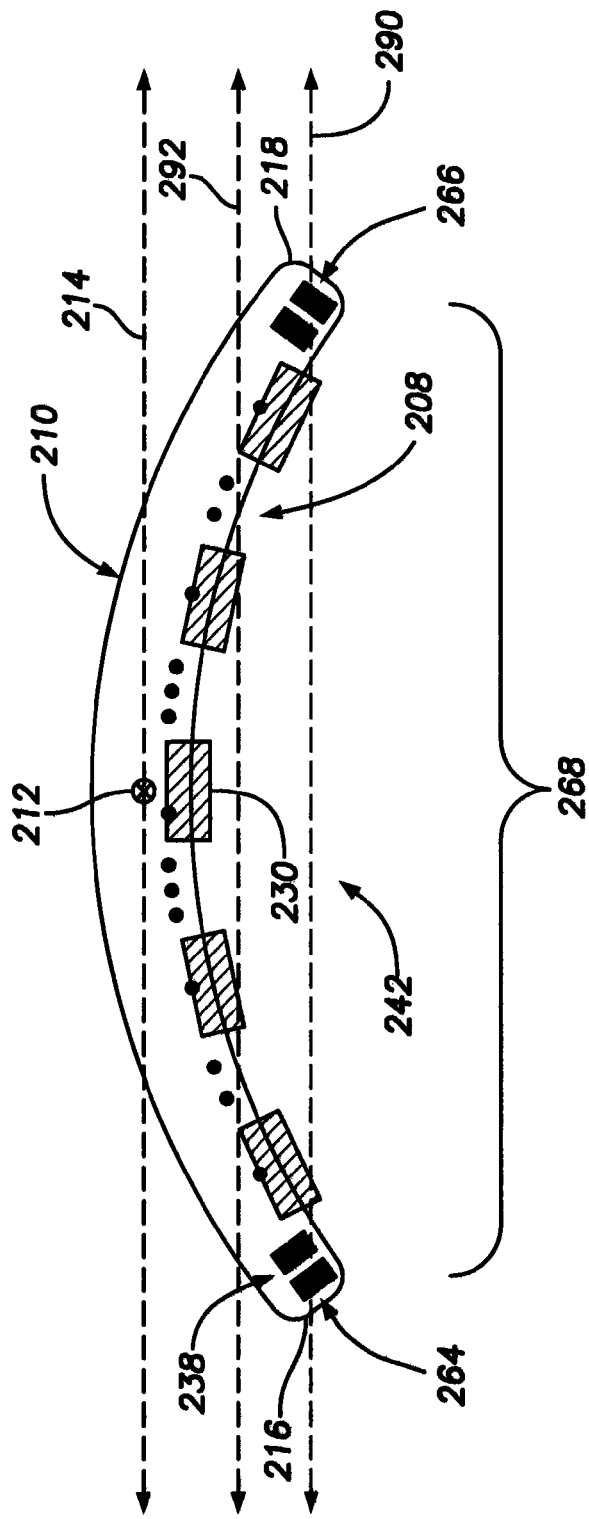
FIG. 5 illustrates a cross-section of the NS device in a flexed condition.

FIG. 4 is a cross-section of the NS device 200 taken along the lines 4-4 in FIG. 3. In FIG. 4, the NS device 200 is in a relaxed condition. FIG. 5 illustrates the cross-section of the NS device 200 in a flexed condition, such as when the NS device 200 is positioned against the dura mater within the epidural space. As shown, the active side 208 is opposite the body side 210 and includes the multi-electrode array 242. The electrodes 230 are configured to interface with the nervous tissue (not shown). Each of the electrodes 230 shown in FIG. 4 is directly coupled to one of the wire conductors 240. FIG. 4 also shows a number of other wire conductors 240 that may electrically couple to the other electrodes 230 of the multi-electrode array 242.

The device body 202 may have a low-profile shape such that the device body 202 is substantially planar. For example, the length 224 (FIG. 3) and the width 226 (FIG. 3) may be significantly larger (e.g., at least 3×, 4×, or 6× greater) than the thickness 225. The device body 202 may substantially coincide with a body plane, such as a plane defined by the lateral and longitudinal axes 214, 212. The body plane is represented by the lateral axis 214 shown in FIG. 4.

In some embodiments, the inductive coil 238 includes a plurality of turns or windings 262. The turns 262 may follow substantially identical paths through the device body 202. The turns 262 may be electrically separated by insulative material that forms part of the device body 262. Sensitivity or effectiveness of the inductive coil 238 for communicating data and/or electrical power through inductive coupling may be based on the number of turns 262 and an area defined by the coil path. The coil path may include substantially linear portions 264, 266 that extend generally parallel to the longitudinal edges 216, 218 (FIG. 3), respectively.

As shown in FIG. 5, the linear portions 264, 266 are separated by an operative width 268 of the coil area. The operative width 268 is the width that partially defines the coil area when the inductive coil 238 is interacting with the primary coil (not shown). In some cases, the operative width 268 may be less than a maximum width of the inductive coil 238 due to the NS device 200 being in the flexed condition.

The inductive coil 238 may surround at least a portion of the multi-electrode array 242. In one embodiment, as shown in FIGS. 3-5, the inductive coil 238 may generally surround the entire multi-electrode array 242. Also shown, the inductive coil 238 may be substantially planar. For instance, in some embodiments, the inductive coil 238 may substantially coincide with the body plane defined by the longitudinal and lateral axes 212, 214 or substantially coincide with a coil plane 290 (FIG. 5) that is oriented parallel to the body plane. As shown, the linear portions 262, 264 of the inductive coil 238 extend along the coil plane 290.

Also shown in FIG. 5, the electrodes 230 of the multi-electrode array 242 are generally aligned along an array plane 292. The array plane 292 may be oriented parallel to the body plane. The array plane 292 may also extend substantially parallel to or substantially coincide with the coil plane 290. As shown in FIG. 5, it is not necessary for each and every electrode 230 to intersect the array plane 292 for the electrodes 230 of the multi-electrode array 242 to be generally aligned along the array plane 292. Instead, the multi-electrode array 242 may have an operative contour such that some of the electrodes 230 intersect the array plane 292, some of the electrodes 230 are above the array plane 292, and some of the electrodes 230 are below the array plane 292.

In the illustrated embodiment, the NS device 200 is configured to flex from the relaxed condition shown in FIG. 4 to the flexed condition shown in FIG. 5, such as when experiencing external forces that change the contour or shape of the NS device 200. In some embodiments, however, the NS device 200 may be formed such that the NS device 200 is biased to have the shape shown in FIG. 5. The NS device 200 may have the shape shown in FIG. 5 when in the relaxed condition. In such embodiments, the shape of the NS device 200 may be based on the anatomical structure(s) that the NS device 200 engages when in operation, such as the dura mater. More specifically, the NS device 200 may be configured to complement the shape of the dura mater. The non-planar shape of the NS device 200 may be provided during the manufacturing of the NS device 200. For instance, the N/S device 200 may be molded within a mold cavity that has the desired shape. Alternatively or in addition to, resilient elements (e.g., harder plastic meshes, fibers, strips, plates, and the like) may be added within the body of the NS device 200. In alternative embodiments, metallic materials may be used. As one specific example, a resilient element may be a plastic mesh that extends laterally and longitudinally across substantially the entire device body 202. Accordingly, resilient element(s) may be configured to bias the NS device 200 into the designated shape. For instance, the resilient element(s) may permit the device body 202 to be flexed into a substantially planar shape, such as the shape shown in FIG. 4, but the resilient element(s) may bias the device body 202 such that the NS device 200 returns to the shape shown in FIG. 5.

Figure 6:
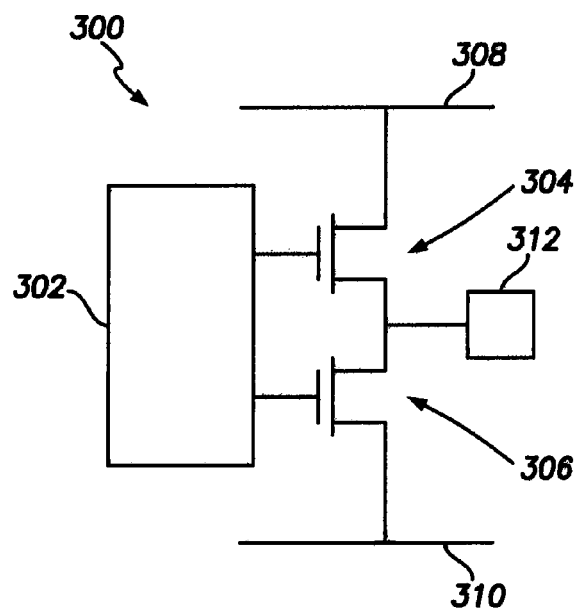
FIG. 6 is an electrical diagram of a cell used for controlling the output to an electrode.

FIG. 6 illustrates a single representative cell 300 for controlling an operating state of an electrode, such as the electrodes 230 (FIG. 3). The cell 300 may be implemented within a multiplexer or other switching circuitry, such as the switching circuitry 142 (FIG. 2) or 233 (FIG. 3), and may be electrically coupled to multiple electrodes. The cell 300 may also be implemented within a single electrode such that, in some embodiments, at least some of the electrodes of the multi-electrode array may contain the cell 300. The cell 300 includes logic circuitry 302 that is configured to control transistors 304, 306 in accordance with a designated sequence or protocol. The transistor 304 is electrically coupled to a power line 308 and is configured to receive electrical current therefrom. The transistor 306 is electrically coupled to a ground line 310. An output 312 is electrically coupled between the transistors 304 and 306. The output 312, in turn, may be electrically coupled to the electrode (not shown).

As set forth herein, the electrodes may be configured to have at least two operating states. In particular embodiments, the electrodes are configured to have one of three operating states. The operating states may be a source state such that the electrode functions as an anode, a sink state such that the electrode functions as an cathode, or an inoperative or inactive state such that the electrode effectively does not supply or draw current. For example, when the electrode is in the source state, the transistor 304 may be closed and the transistor 306 may be open such that current flows from the power line 308 through the circuitry to the output 312. When the electrode is in the sink state, the transistor 304 may be open and the transistor 306 may be closed such that current flows from the output 312 to the ground line 310. When the electrode is in an inoperative state, each of the transistors 304, 306 are opened. In such embodiments, the cell 300 has a high impedance such that current does not effectively flow through the output 312 in either direction. It is noted, however, that the cell 300 is only representative of how circuitry may be configured to control the operating state of an electrode. Other circuits may be used in other embodiments.

In some embodiments, the switching circuitry 142 or 233 may have a plurality of the cells 300 therein. In such embodiments, each of the outputs 312 may be electrically coupled to one of the wire conductors 240 (FIG. 3). Accordingly, the output 312 may be selectively controlled to supply or draw current through the respective wire conductor 240 or to effectively render the wire conductor inoperative with high impedance. For example, the NS device 200 in FIG. 3 includes sixteen (16) electrodes 230 that receive current directly from the switching circuitry 233. As such, the NS device 200 has sixteen (16) wire conductors 240.

Figure 7:
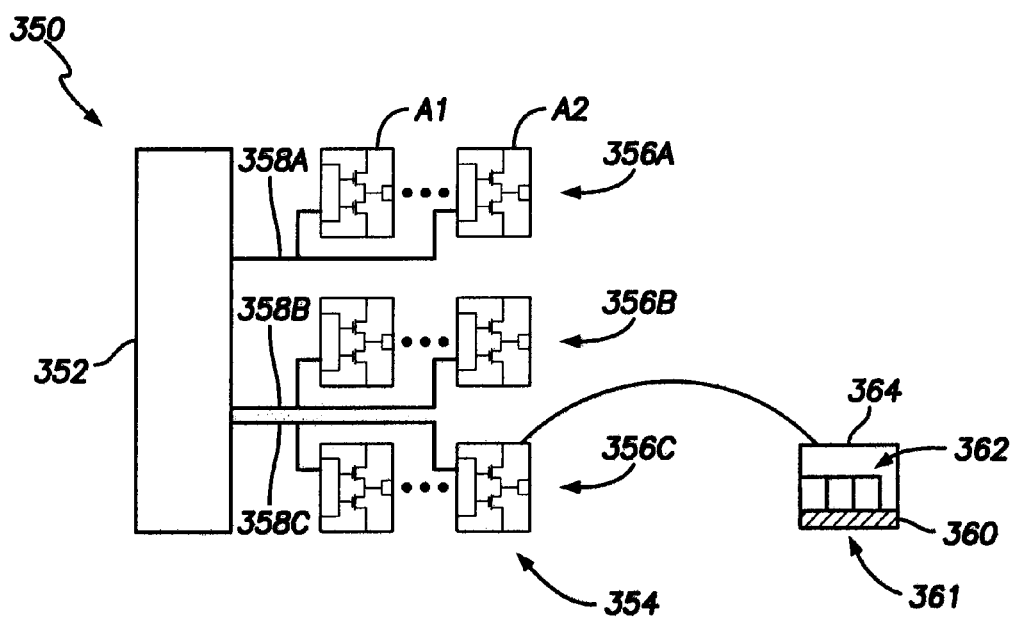
FIG. 7 illustrates an electrical diagram for generating electric fields proximate to nervous tissue in accordance with an embodiment.

FIG. 7 illustrates an electrical diagram 350 for generating electric fields proximate to nervous tissue in accordance with an embodiment. As shown, switching circuitry 352 is electrically coupled to electrodes 354. The electrodes are arranged in columns 356A-356C. In FIG. 7, only two electrodes 354 are shown in each column, but it is understood that each column may include more than two electrodes. Each of the electrodes 354 of a single column is electrically coupled to the switching circuitry 352 through a common (i.e., the same) control line. For example, the electrodes 354 of the column 356A are electrically coupled to a control line 358A, the electrodes 354 of the column 356B are electrically coupled to a control line 358B, and the electrodes 354 of the column 356C are electrically coupled to a control line 358C. Although not shown, each of the electrodes may be electrically coupled to a power line and a ground line. The power and ground lines may electrically couple to a combination of the electrodes 354.

In some embodiments, more than one control line may be electrically coupled to the electrodes of a column, and the electrodes may be controlled in accordance with a designated protocol. For example, the electrodes 354 of the column 356A may be electrically coupled to two control lines. A first control line may be a data line and a second control line may be a clock line. By way of example only, the first and second control lines may be operated in accordance with inter-integrated circuit protocol (or I²C protocol).

With respect to the electrodes 354 of the column 356A, the switching circuitry 352 is configured to communicate control signals through the control line 358A such that each of the electrodes 354 receives the same control signals. Such communication may be referred to as broadcasting because each of the electrodes 354 in the same column receives the same control signals. The control signals may represent, among other things, operating states of the electrodes 354 and addresses (or identifiers) that designate the electrodes 354. Each address may be associated with or correlate to an operating state. As such, the control signals may include instructions for each of the electrodes within the same column. As one example, the control signals may instruct that electrode A1 operate as an anode and that electrode A2 operate as a cathode.

A side view of a representative electrode 354 is also shown in FIG. 7. The electrodes 354 may include a housing 364 (e.g., a ceramic housing) that is configured to hermetically seal internal circuitry of the electrode 354. The housing 364 may be mounted to a stimulating element 360 that is electrically coupled to logic circuitry 362. The logic circuitry 362 may be disposed within a cavity formed by the housing 364. The logic circuitry 362 may be electrically coupled to one of the control lines, a ground line (not shown), and a power line (not shown). The logic circuitry is also coupled to the stimulating element 360 for controlling the operating state of the stimulating element 360. The stimulating element 360 includes a surface 361 that is configured to interface with the nervous tissue.

The logic circuitry 362 is configured to receive control signals (e.g., from the switching circuitry 352) through the corresponding control line and identify the instructed operating state for the corresponding electrode 354 based on the address that is designated to the electrode 354. For example, the logic circuitry 362 of the electrode that is designated as A1 may analyze the control signals to identify the operating state that is associated with the address A1 and disregard the operating state associated with other addresses (e.g., A2). In response to the control signals, the logic circuitry 362 in the electrode A1 may change or maintain the operating state. During operation, each of the electrodes 354 is capable of drawing power from a power line to operate as a source or using a ground line to operate as a sink. In such embodiments, fewer wire conductors may be used than embodiments that utilize a single wire conductor for each electrode.

Figure 8:
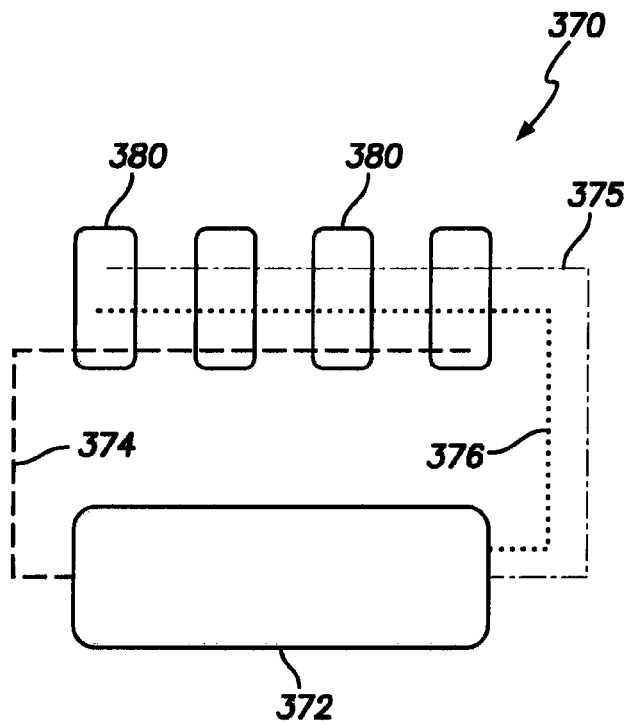
FIG. 8 illustrates another electrical diagram for generating electric fields proximate to nervous tissue in accordance with an embodiment.

FIG. 8 illustrates another electrical diagram 370 for generating electric fields proximate to nervous tissue in accordance with an embodiment. As shown, the electrical diagram 370 includes switching circuitry 372, a plurality of wire conductors 374-376, and electrodes 380. The wire conductors include a power line 374, a ground line 375, and a control line 376. Each of the power line 374, the ground line 375, and the control line 376 is electrically coupled to each of the electrodes 380 in FIG. 8. Although only four electrodes 380 are shown in FIG. 4, embodiments may include fewer or more electrodes (e.g., two, eight, twelve, sixteen, or more). During operation, each of the electrodes 380 is capable of drawing power from the power line 374 to operate as a source or using the ground line 375 to operate as a sink. Similar to above, the switching circuitry 372 may broadcast control signals that represent addresses and operating states associated with the addresses. Each of the electrodes 380 may be designated with one of the addresses and may be configured to identify the operating state associated with the respective address. Accordingly, in some embodiments, the switching circuitry 372 may be capable of selectively operating the electrodes using only three wire conductors.

Figure 9:
FIG. 9 is a flowchart illustrating a method of manufacturing a NS device.

FIG. 9 is a flowchart illustrating a method 400 of manufacturing a NS device. The method 400, for example, may employ structures or aspects of various embodiments (e.g., systems and/or methods) discussed herein. For example, the NS device may be similar to the NS device 102 (FIG. 1) or the NS device 200 (FIG. 3) or may include other features, such as those described or referenced herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of manufacturing an NS device. Other methods may be used.

The method 400 may include positioning (at 402) electrodes with respect to each other to form a multi-electrode array. For example, the electrodes may be positioned within a mold relative to one another in positions that are identical or similar to the electrode positions in the fully formed NS device. The electrodes may be positioned to form a one-dimensional or two-dimensional array of the electrodes.

The method 400 may also include providing (at 404) an electronic sub-system (or pulse generator), such as an inductive coil, power source, memory, control unit, current/voltage source(s), or switching circuitry. The providing (at 404) may include positioning one or more components of the electronic sub-system relative to the multi-electrode array within the mold. For example, one or more of the power source, memory, control unit, current/voltage source(s), or switching circuitry may be positioned at one end of the multi-electrode array. When provided (at 404), the components may be operably coupled such that the one or more components may communicate and interact with one another as described herein.

As noted above, one or more of the components of the electronic sub-system may be found in a single piece of hardware. For example, the control unit may include the current/voltage source(s) and switching circuitry. In some embodiments, the electronic sub-system is pre-assembled. For example, two or more of the power source, memory, control unit, current/voltage source(s), or switching circuitry may be coupled to one another. In some embodiments, the components may be within a common housing.

The method 400 may also include electrically coupling (at 406) the electrodes to the electronic sub-system through wire conductors. Electrically coupling (at 406) may include directly coupling a component to an electrode. For example, each electrode in the array may be directly coupled to the electronic sub-system or, more specifically, the switching circuitry. Alternatively, electrically coupling (at 406) may include indirectly coupling one or more electrodes. For example, as described above, one or more electrodes may be common electrodes that are electrically coupled to base electrodes through bridge conductors. The coupling of a wire conductor to another component may be performed through one or more manufacturing processes, such as soldering, welding, wire bonding, etching, or using a conductive adhesive.

The method 400 may also include forming (at 408) a device body that at least partially surrounds the electronic sub-system. By way of one example only, an insulative material (in fluid form) may be injected into the mold containing the electrodes, wire conductors, and the electronic sub-system. The insulative material may be, for example, one or more of the materials listed herein. The forming (408) may be a single step or may include multiple steps. For example, one or more components of the electronic sub-system may be pre-formed by overmolding the components with an insulative material(s). The overmolded components may be positioned relative to the electrodes and wire conductors. The wire conductors may then be attached to, for example, the switching circuitry prior to a second overmolding process. In some embodiments, the device body, including the electronic sub-system and the wire conductors, are collectively sized and shaped to be disposed within an epidural space of a patient.

In an embodiment, a leadless neurostimulation (NS) device is provided that includes a device body having opposite first and second ends and an active side that extends between the first and second ends. The NS device also includes electrodes forming a multi-electrode array along the active side of the device body. The multi-electrode array is configured to interface with nervous tissue in an epidural space of a patient and generate electric fields along the nervous tissue. The NS device also includes an electronic sub-system provided within the device body. The electronic sub-system includes switching circuitry, a power source, and an inductive coil operably coupled to the power source. The electronic sub-system is configured to provide electrical pulses to the multi-electrode array for generating the electric fields. The inductive coil is configured to receive electrical power through inductive coupling with an external coil to charge the power source. The device body, including the inductive coil coupled thereto, is sized and shaped to be disposed within the epidural space of the patient.

In one aspect, the NS device may be a wireless lead that is configured to be disposed entirely within the epidural space. For example, the inductive coil may also be configured to communicate data with an external monitoring system.

In another aspect, the device body may be a low-profile substantially planar body that coincides with lateral and longitudinal axes that are perpendicular to each other. The inductive coil may be substantially planar and extending along the lateral and longitudinal axes.

In another aspect, the inductive coil extends along a path. A majority of the path may extend alongside edges of the device body.

In another aspect, the device body is oriented with respect to a longitudinal axis and a lateral axis that are perpendicular to each other. The longitudinal axis extends between the first and second ends. The multi-electrode array may constitute a two-dimensional array having a plurality of the electrodes positioned along the lateral axis and a plurality of the electrodes positioned along the longitudinal axis.

In another aspect, the electrodes of the multi-electrode array may be generally aligned along an array plane. The inductive coil may be shaped to extend generally along a coil plane. The coil plane may extend substantially parallel to or substantially coincides with the array plane.

In another aspect, each of the electrodes of at least a sub-array of the multi-electrode array is electrically coupled to the electronic sub-system through a single wire conductor. The electronic sub-system selectively controls each of the electrodes coupled to the wire conductors to function as an anode, a cathode, or an inoperative element through the respective wire conductor.

In another aspect, the multi-electrode array may be electrically coupled to the electronic sub-system through a plurality of wire conductors. The plurality of wire conductors may include a power line, a ground line, and a control line, wherein each of the power, ground, and control lines may directly couple to a plurality of the electrodes.

In another aspect, the electronic sub-system may be configured to broadcast control signals to at least a sub-array of the multi-electrode array such that each electrode of the sub-array receives the control signals. The control signals may represent multiple addresses and operating states that correspond to the addresses. Each of the electrodes may be designated with one of the addresses. Each of the electrodes of the sub-array may be configured to determine the operating state of the respective electrode from the control signals based on the address that is designated with the electrode.

In an embodiment, a leadless neurostimulation (NS) device is provided that includes a device body having opposite first and second ends and an active side that extends between the first and second ends. The NS device also includes electrodes forming a multi-electrode array along the active side of the device body. The multi-electrode array is configured to interface with nervous tissue in an epidural space of a patient and generate electric fields along the nervous tissue. The NS device also includes an electronic sub-system provided within the device body and wire conductors that extend through the device body and electrically couple the multi-electrode array to the electronic sub-system. The electronic sub-system is configured to control the electrodes to generate electric fields proximate to the nervous tissue, wherein the device body, including the electronic sub-system, is sized and shaped to be disposed within an epidural space of the patient.

In one aspect, each of the electrodes of at least a sub-array of the multi-electrode array may be electrically coupled to the electronic sub-system through only one of the wire conductors. The electronic sub-system may selectively control each of the electrodes of the sub-array to function as an anode, a cathode, or an inoperative element through the respective wire conductor.

In another aspect, the electrodes may be electrically coupled to the electronic sub-system through a plurality of the wire conductors. The wire conductors may include a control line, a power line, and a ground line, wherein the control line, the power line, and the ground line may each be electrically coupled to at least some of the electrodes.

In another aspect, the electronic sub-system may be configured to broadcast control signals to at least a sub-array of the multi-electrode array such that each electrode of the sub-array receives the control signals. The control signals may represent multiple addresses and operating states that correspond to the addresses. Each of the electrodes may be designated with one of the addresses, wherein each of the electrodes of the sub-array may be configured to determine the operating state of the respective electrode from the control signals based on the address that is designated with the electrode.

In another aspect, the electrodes may include a base electrode and a common electrode that is electrically coupled to the base electrode through a bridge conductor. The common electrode may be electrically coupled to the electronic sub-system through the bridge conductor and the base electrode.

In another aspect, the electronic sub-system may include an inductive coil that is operably coupled to the power source. The inductive coil may be sized and shaped to be disposed within the epidural space with the device body and the electronic sub-system. In particular embodiments, the inductive coil may surround at least a sub-array of the multi-electrode array.

In an embodiment, a method of manufacturing a leadless neurostimulation (NS) device is provided. The method includes positioning electrodes with respect to each other to form a multi-electrode array and providing an electronic sub-system including switching circuitry, a power source, and an inductive coil that is operably coupled to the power source. The method also includes electrically coupling the electrodes to the electronic sub-system through wire conductors and forming a device body that at least partially surrounds the switching circuitry, the power source, and the inductive coil. The electrodes are positioned along an active side of the device body. The device body, the switching circuitry, the power source, and the inductive coil are collectively sized and shaped to be disposed within an epidural space of a patient.

In one aspect, the electrodes may form a two-dimensional array having a plurality of the electrodes positioned along a lateral axis and a plurality of the electrodes positioned along a longitudinal axis. The lateral and longitudinal axes may extend perpendicular to each other, wherein the inductive coil generally surrounds at least a sub-array of the multi-electrode array. In particular embodiments, the NS device constitutes a paddle lead.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

The following claims recite aspects of certain embodiments of the inventive subject matter and are considered to be part of the above disclosure.

What is claimed is:

1. A leadless neurostimulation (NS) device comprising:
a device body having opposite first and second ends and an active side that extends between the first and second ends;
electrodes forming a multi-electrode array along the active side of the device body, the multi-electrode array configured to interface with nervous tissue in an epidural space of a patient and generate electric fields along the nervous tissue; and
an electronic sub-system provided within the device body, the electronic sub-system comprising a switching circuitry, a power source, and an inductive coil operably coupled to the power source, the electronic sub-system configured to provide electrical pulses to the multi-electrode array for generating the electric fields, the inductive coil configured to receive electrical power through inductive coupling with an external coil to charge the power source, wherein the device body, including the inductive coil coupled thereto, is sized and shaped to be disposed within the epidural space of the patient.

2. The NS device of claim 1, wherein the device body is wireless and is configured to be disposed entirely within the epidural space.

3. The NS device of claim 2, wherein the inductive coil is also configured to communicate data with an external monitoring system.

4. The NS device of claim 1, wherein the device body is a low-profile substantially planar body that coincides with lateral and longitudinal axes that are perpendicular to each other, the inductive coil being substantially planar and extending along the lateral and longitudinal axes.

5. The NS device of claim 1, wherein the inductive coil extends along a path, a majority of the path being adjacent to edges of the device body.

6. The NS device of claim 1, wherein the device body is oriented with respect to a longitudinal axis and a lateral axis that are perpendicular to each other, the longitudinal axis extending between the first and second ends, wherein the multi-electrode array constitutes a two-dimensional array having a plurality of the electrodes positioned along the lateral axis and a plurality of the electrodes positioned along the longitudinal axis.

7. The NS device of claim 1, wherein the electrodes of the multi-electrode array are generally aligned along an array plane, the inductive coil being shaped to extend generally along a coil plane, wherein the coil plane extends substantially parallel to or substantially coincides with the array plane.

8. The NS device of claim 1, wherein each of the electrodes of at least a sub-array of the multi-electrode array is electrically coupled to the electronic sub-system through a single wire conductor, the electronic sub-system selectively controlling each of the electrodes coupled to the wire conductors to function as an anode, a cathode, or an inoperative element through the respective wire conductor.

9. The NS device of claim 1, wherein the multi-electrode array is electrically coupled to the electronic sub-system through a plurality of wire conductors, the plurality of wire conductors including a power line, a ground line, and a control line, wherein each of the power, ground, and control lines directly couples to a plurality of the electrodes.

10. The NS device of claim 1, wherein the electronic sub-system is configured to broadcast control signals to at least a sub-array of the multi-electrode array such that each electrode of the sub-array receives the control signals, the control signals representing multiple addresses and operating states that correspond to the addresses, each of the electrodes being designated with one of the addresses, wherein each of the electrodes of the sub-array is configured to determine the operating state of the respective electrode from the control signals based on the address that is designated with the electrode.

11. A leadless neurostimulation (NS) device comprising:
a device body having opposite first and second ends and an active side that extends between the first and second ends;
electrodes forming a multi-electrode array along the active side of the device body, the multi-electrode array configured to interface with nervous tissue in an epidural space of a patient and generate electric fields along the nervous tissue;
an electronic sub-system provided within the device body; and
wire conductors that extend through the device body and electrically couple the multi-electrode array to the electronic sub-system, the electronic sub-system configured to control the electrodes to generate electric fields proximate to the nervous tissue, wherein the device body, including the electronic sub-system, is sized and shaped to be disposed within an epidural space of the patient.

12. The NS device of claim 11, wherein each of the electrodes of at least a sub-array of the multi-electrode array is electrically coupled to the electronic sub-system through only one of the wire conductors, the electronic sub-system selectively controlling each of the electrodes of the sub-array to function as an anode, a cathode, or an inoperative element through the respective wire conductor.

13. The NS device of claim 11, wherein the electrodes are electrically coupled to the electronic sub-system through a plurality of the wire conductors, the wire conductors including a control line, a power line, and a ground line, wherein the control line, the power line, and the ground line are each electrically coupled to at least some of the electrodes.

14. The NS device of claim 11, wherein the electronic sub-system is configured to broadcast control signals to at least a sub-array of the multi-electrode array such that each electrode of the sub-array receives the control signals, the control signals representing multiple addresses and operating states that correspond to the addresses, each of the electrodes being designated with one of the addresses, wherein each of the electrodes of the sub-array is configured to determine the operating state of the respective electrode from the control signals based on the address that is designated with the electrode.

15. The NS device of claim 11, wherein the electrodes include a base electrode and a common electrode that is electrically coupled to the base electrode through a bridge conductor, the common electrode being electrically coupled to the electronic sub-system through the bridge conductor and the base electrode.

16. The NS device of claim 11, wherein the electronic sub-system includes an inductive coil operably coupled to the power source, the inductive coil sized and shaped to be disposed within the epidural space with the device body and the electronic sub-system.

17. The NS device of claim 16, wherein the inductive coil surrounds at least a sub-array of the multi-electrode array.

18. A method of manufacturing a leadless neurostimulation (NS) device, the method comprising:
positioning electrodes with respect to each other to form a multi-electrode array;
providing an electronic sub-system including switching circuitry, a power source, and an inductive coil that is operably coupled to the power source;
electrically coupling the electrodes to the electronic sub-system through wire conductors; and
forming a device body that at least partially surrounds the switching circuitry, the power source, and the inductive coil, the electrodes being positioned along an active side of the device body, wherein the device body, the switching circuitry, the power source, and the inductive coil are collectively sized and shaped to be disposed within an epidural space of a patient.

19. The method of claim 18, wherein the electrodes form a two-dimensional array having a plurality of the electrodes positioned along a lateral axis and a plurality of the electrodes positioned along a longitudinal axis, the lateral and longitudinal axes extending perpendicular to each other, wherein the inductive coil generally surrounds at least a sub-array of the multi-electrode array.

20. The method of claim 19, wherein the NS device constitutes a paddle lead.

\* \* \* \* \*